US009340471B2

(12) United States Patent
Al-Qahtani et al.

(10) Patent No.: US 9,340,471 B2
(45) Date of Patent: May 17, 2016

(54) METALATED LIGAND, CATALYST COMPOSITION, AND USE THEREOF IN THE OLIGOMERIZATION OF ETHYLENE

(71) Applicant: SAUDI BASIC INDUSTRIES CORPORATION, Riyadh (SA)

(72) Inventors: Abdullah Mohammad Al-Qahtani, Riyadh (SA); Mohammed H. Al-Hazmi, Riyadh (SA); Uwe Rosenthal, Lambrechtshagen (DE); Bernd H. Müller, Rostock (DE); Normen Peulecke, Rostock (DE); Marco Harff, Munich (DE); Anina Wöhl, Munich (DE); Andreas Meiswinkel, Munich (DE); Heinz Bölt, Wolfratshausen (DE); Wolfgang Müller, Munich (DE)

(73) Assignees: SAUDI BASIC INDUSTRIES CORPORATION, Riyadh (SA); LINDE AG (DE)

( * ) Notice: Subject to any disclaimer, the term of this patent is extended or adjusted under 35 U.S.C. 154(b) by 0 days.

(21) Appl. No.: 14/176,535

(22) Filed: Feb. 10, 2014

(65) Prior Publication Data
US 2014/0228608 A1 Aug. 14, 2014

(30) Foreign Application Priority Data
Feb. 11, 2013 (EP) .................................. 13154784

(51) Int. Cl.
| C07F 9/50 | (2006.01) |
| C07C 2/30 | (2006.01) |
| C07F 11/00 | (2006.01) |
| B01J 31/14 | (2006.01) |
| B01J 31/02 | (2006.01) |
| B01J 31/18 | (2006.01) |
| C07C 2/36 | (2006.01) |

(52) U.S. Cl.
CPC .............. *C07C 2/30* (2013.01); *B01J 31/0231* (2013.01); *B01J 31/0239* (2013.01); *B01J 31/0271* (2013.01); *B01J 31/143* (2013.01); *B01J 31/1885* (2013.01); *C07C 2/36* (2013.01); *C07F 9/5004* (2013.01); *C07F 9/5045* (2013.01); *C07F 9/5054* (2013.01); *C07F 11/00* (2013.01); *B01J 2231/20* (2013.01); *B01J 2531/0205* (2013.01); *B01J 2531/11* (2013.01); *B01J 2531/22* (2013.01); *B01J 2531/26* (2013.01); *B01J 2531/31* (2013.01); *B01J 2531/62* (2013.01); *C07C 2527/10* (2013.01); *C07C 2531/14* (2013.01); *C07C 2531/24* (2013.01); *Y02P 20/52* (2015.11)

(58) Field of Classification Search
USPC ........ 585/513; 502/117, 167; 556/14; 564/12
See application file for complete search history.

(56) References Cited

U.S. PATENT DOCUMENTS

| 2008/0182951 A1* | 7/2008 | Ackerman et al. ............ 526/154 |
| 2014/0228580 A1 | 8/2014 | Rosenthal et al. |
| 2014/0228594 A1 | 8/2014 | Rosenthal et al. |

FOREIGN PATENT DOCUMENTS

| EP | 2239056 A1 | 10/2010 |
| EP | 2239056 B1 | 7/2011 |
| WO | 0204119 A1 | 1/2002 |
| WO | 2009006979 A2 | 1/2009 |
| WO | WO 2010/115520 | * 10/2010 |

OTHER PUBLICATIONS

Peitz, S.; Peulecke, N.; Aluri, B.R.; Mailer, B.H.; Spannenberg, A.; Rosenthal, U.; Al-Hazmi, M.H.; Mosa, F.M.; Wöhl, A.; Müller, W. "Metalation and Transmetalation Studies on Ph2PN(iPr)P(Ph)N(iPr)(H) for Selective Ethene Trimerization to 1-Hexene". Organometallics (2010), 29, 5263-5268.*
Dulai, A.; McMullin, C. L.; Tenza, K.; Wass, D. F. "N,N-Bis(diphenylphosphino)diaminophenylphosphine Ligands for Chromium-Catalyzed Selective Ethylene Oligomerization Reactions" Organometallics (2011), 30, 935-941.*
Peitz, S.; Peulecke, N.; Aluri, B. R.; Hansen, S.; Muller, B. H.; Spannenberg, A.; Rosenthal, U.; Al-Hamzi, M. H.; Mosa, F. M.; Wohl, A.; Muller, W. "A selective Chromium Catalyst System for the Trimerization of Ethene and Its Coordination Chemistry", Eur. J. Inorg. Chem. (2010), 1167-1171.*
Peitz, S.; Peulecke, N.; Aluri, B.R.; Muller, B.H.; Spannenberg, A.; Rosenthal, U.; Al-Hazmi, M.H.; Mosa, F.M.; Wöhl, A.; Muller, W. "Metalation and Transmetalation Studies on Ph2PN(iPr)P(Ph)N(iPr)H for Selective Ethene Trimerization to 1-Hexene"; Organometallics, (2010), 29, pp. 5263-5268.*
European Search Report for EP13154794 mailed Mar. 7, 2013, 1 page.
Written Opinion of the International Searching Authority for PCT/IB2014/058921 mailed Apr. 16, 2014, 6 pages.
Written Opinion of the Intl Searching Authority for PCT/IB2014/058917 mailed Apr. 14, 2014, 10 pages.
Aluri, B, et al., "Coordination chemistry of new selective ethylene trimerisation ligand Ph2PN(iPr)P(Ph)NH(R)(R=iPr, Et) and tests in catalysis", Dalton Transactions, 39, 7911-7920 (2010).
Dulai, Arminderjit, et al., "N,N'-Bis(diphenylphosphino)diaminophenylphosphine Ligands for Chromium-Catalyzed Selective Ethylene Oligomerization Reactions", Organometallics, 30, 935-941 (2011).
European Search Report; EP13154784.6-1352; Date of completion of the search Aug. 30, 2013; 14 pages.
Muller, B, et al, "Synthesis and Reactions of the Homoleptic Chromium (II) Bis-amide [Ph 2 PN(i Pr)P(Ph)N(iPr)-]-]2Cr with Relevance to a Selective Catalytic Ethene Trimerization System to 1-Hexene", Organometallics, 31, 3695-3699 (2012).

(Continued)

*Primary Examiner* — In Suk Bullock
*Assistant Examiner* — Aaron Pierpont
(74) *Attorney, Agent, or Firm* — Cantor Colburn LLP

(57) ABSTRACT

A process for oligomerization of ethylene, comprising subjecting a catalyst composition to a gas phase of ethylene and conducting an oligomerization, wherein the catalyst composition comprises (a) a chromium compound, (b) a metalated ligand, and (c) an activator or cocatalyst; and catalyst composition as well as a metalated ligand.

13 Claims, No Drawings

(56) References Cited

OTHER PUBLICATIONS

International Search Report; International Application No. PCT/IB2014/058917; Feb. 11, 2014; 7 pages.

International Search Report; Internatonal Application No. PCT/IB2014/058919; Feb. 11, 2014; 4 pages.

Written Opinion; International Application No. PCT/IB2014/058919; Nov. 2, 2014; 6 pages.

International Search Report; International Application No. PCT/IB2014/058921; Feb. 11, 2014; 4 pages.

Peitz, Stephan, et al. "Activation and Deactivation by Temperature: Behavior of Ph2PN(iPr)P(Ph)N(iPr)H in the Presence of Alkylaluminum Compounds Relevant to Catalystic Selective Ethene Trimerization", Chemisty—A European Journal, vol. 16, No. 40, 12127-12132 (Oct. 2011).

Peitz, Stephan, "A Selective Chromium Catalyst System for the Trimerization of Ethene and Its Coorination Chemistry", European Journal of Inorganic Chemistry, 1167-1171 (Feb. 2010).

Peitz, Stephan, et al. "Heterobimetallic Al—Cl—Cr Intermediates with Relevance to the Selective Catalytic Ethene Trimerization Systems Consisting of CrCl3(THF)3, the Aminophosphorus Ligands Ph2PN(R)P(Ph(N(R)H, and Triethylaluminum", Organometalics 30, 2364-2370 (2011).

Peitz, S, et al., "Metalation and Trasmetalation Studies on Ph2PN(iPr)P(Ph)N(iPr)H for Selective Ethene Trimerization to 1-Hexene", Organometallics, 29, 5263-5268 (2010).

International Preliminary Report on Patentability and Written Opinion for International Application No. PCT/IB2014/058919, Application Filing Date—Feb. 11, 2014, Date of Mailing Aug. 20, 2015, seven pages.

International Preliminary Report on Patentability and Written Opinion for International Application No. PCT/IB2014/058917; Application Filing Date Feb. 11, 2014; Date of Mailing Aug. 20, 2015, 11 pages.

International Preliminary Report on Patentability and Written Opinion for International Application No. PCT/IB2014/058921, Application Filing Date Feb. 11, 2014, Date of Mailing Aug. 20, 2015, seven pages.

International Search Report for International Application No. PCT/IB2015/050077; Application Filing Date—Jan. 5, 2015; Date of Mailing—Aug. 11, 2015, six pages.

Written Opinion for International Application No. PCT/IB2015/050077; Application Filing Date—Jan. 5, 2015; Date of Mailing—Aug. 11, 2015, seven pages.

* cited by examiner

METALATED LIGAND, CATALYST COMPOSITION, AND USE THEREOF IN THE OLIGOMERIZATION OF ETHYLENE

BACKGROUND

The present invention relates to a process for oligomerization of ethylene, a catalyst composition used in the oligomerization, as well as a metalated ligand used in that catalyst composition.

Compounds having the general structure PNPNH are well known ligand systems which can be successfully used in a catalyst for the oligomerization of ethylene. Here, they function as ligands to be reacted with, preferably, chromium catalysts. Together with a suitable cocatalyst such a system is effective in the di-, tri- and/or tetramerization of ethylene.

For example, EP 2 239 056 B1 describes a catalyst composition and a process for the di-, tri- and/or tetramerization of ethylene. The catalyst composition comprises a chromium compound, a ligand of the general structure $R_1R_2P$—N($R_3$)—P($R_4$)—N($R_5$)—H and a co-catalyst acting as activator. The ligand's substituents $R_1$, $R_2$, $R_3$, $R_4$, and $R_5$ are independently selected from a number of functional groups, comprising (among others) $C_1$-$C_{10}$-alkyl, aryl and substituted aryl. The chromium source is selected from $CrCl_3(THF)_3$, Cr(III)acetylacetonate, Cr(III)octanoate, Cr-hexacarbonyl, Cr(III)-2-ethylhexanoate, and (benzene)tricarbonyl-chromium, where THF is tetrahydrofuran. The co-catalyst or activator is selected from trimethylaluminum, triethylaluminum, triisopropylaluminum, triisobutylaluminum, ethylaluminum sesquichloride, diethylaluminum chloride, ethylaluminum dichloride, methylaluminoxane ("MAO"), or a combination comprising at least one of the foregoing, preferably toluene.

A preferred choice of catalyst constituents comprises $CrCl_3(THF)_3$ as chromium source, triethylaluminum as activator, and $(Ph)_2P$—N(i-Pr)—P(Ph)-N(i-Pr)—H as ligand for the catalytically active complex as shown below wherein Ph is a phenyl group and i-Pr is an isopropyl group). This ligand features the typical PNPN—H-backbone, which is why this class of compounds, regardless of the precise nature of its substituents, is often referred to as a "PNPNH-ligand."

WO 2009/006979 A2 describes essentially modified catalyst systems of the general type already disclosed in EP 2 239 056 B1. These modified systems take advantage from the same PNPNH-type ligands. However, now a "modifier" is added to the system, selected from (but not limited to) ammonium or phosphonium salts of the type $[H_4E]X$, $[H_3ER]X$, $[H_2ER_2]X$, $[HER_3]X$, or $[ER_4]X$ wherein E is N or P, X is Cl, Br or I, and R is alkyl, cycloalkyl, acyl, aryl, alkenyl, alkynyl, and the like.

Preferred embodiments disclosed in WO 2009/006979 A2 involve, for instance, modifiers such as tetraphenylphosphonium chloride, tetraethylammonium chloride monohydrate, triethylamine hydrochloride etc. Also, as a "type $[ER_4]X$" modifier, dodecyltrimethylammonium chloride can advantageously be used, due to its low price, abundant supply, and good solubility in the reaction solution.

In fact, the specifically designed coordination behaviour of the PNPNH ligands is largely the origin of the high selectivities of the catalytically active chromium complexes. Clearly, the high product selectivities are of great importance for the economic viability of the technical process.

Of course, a high selectivity directly results in a minimization of undesired side products in the technical oligomerization process. It is therefore evident that the "key ingredients" of the catalyst have to be produced on technical scale with the highest possible quality.

Further, especially the preparation method for the ligand of the catalyst composition shall be cost effective, easy, and fast and shall result in high purities.

The laboratory procedure for the preparation of the PNPNH ligand gives a material of good quality.

Using the ligand from the laboratory bench-scale synthesis in standardised catalytic tests of the ethylene trimerization to 1-hexene, it is easily possible to obtain overall 1-hexene yields of 91-93 weight percent at 1-hexene purities of 99.0-99.3% with hardly any detectable wax/polymer formation.

When being transferred to technical scale, however, this laboratory procedure regularly needs some modifications so as to meet the requirements imposed by boundary conditions in a technical environment. For example, in order to avoid hot spots in the reaction mass, it might be advisable to change the dosing sequence and/or dosing speed of some of the ingredients. Furthermore, reaction temperatures as low as −40° C. will, most likely, be unfavourable or even not feasible on technical scale. Moreover, solvents may have to be recycled, resulting in the need to vary the nature of the solvent or to use solvent mixtures.

Even after optimization of the ligand's production process on technical scale, it does not seem to be possible to reach a ligand quality, i.e., purity, comparable to the product synthesized using the laboratory procedure.

One of the most severe problems in all known technical-scale ethylene oligomerization processes is the formation of long-chain by-products such as waxes and polyethylene. Clearly, this leads to frequent fouling of equipment such as reactor inner surfaces, heat exchangers, etc. Moreover, wax or polymer formation can lead to plugging of tubing, valves, pumps, and other equipment, making frequent plant shut downs for purging/cleaning and maintenance of equipment necessary.

The measured formation rate of waxes/polymers has to be considered in the design of a commercial ethylene oligomerization plant. Adequate minimization measures and handling procedures for these undesired by-products are inevitable in order to allow for commercially successful plant operation.

Having in mind that, as already pointed out above, a high selectivity results directly in a minimization of undesired side products in this technical process, the "key ingredients," i.e. especially the ligand, has to be produced on technical scale with the highest possible quality.

It is therefore desirable to provide a process for oligomerization of ethylene, which allows use of a catalyst composition comprising a ligand which can be prepared in high purity in a safe and easy manner and results in a process with low wax/polymer formation rates. It is a further object to provide a respective catalyst composition which can be successfully utilized in the oligomerization of ethylene.

Further, it would be advantageous provide a metalated ligand that can be employed in the catalyst composition as well as a method for its preparation.

SUMMARY

Disclosed herein is a process for oligomerization of ethylene, comprising contacting a catalyst composition with a gas phase of ethylene under conditions effective to oligomerize the ethylene, wherein the catalyst composition comprises
   (a) a chromium compound,
   (b) a metalated PNPNH compound, wherein the PNPNH compound is of the formula

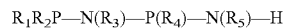

wherein $R_1$, $R_2$, $R_3$, $R_4$ and $R_5$ are independently selected from halogen, amino, trimethylsilyl, $C_1$-$C_{10}$-alkyl, substituted $C_1$-$C_{10}$-alkyl, $C_6$-$C_{20}$-aryl and substituted $C_6$-$C_{20}$-aryl, or any cyclic derivative wherein at least one of the P or N atoms of the PNPN—H structure is a member of a ring system, the ring system being formed from one or more constituent compounds of the PNPNH-structure by substitution, and (c) an activator or cocatalyst.

In another embodiment,

In another embodiment, a catalyst composition for oligomerization of ethylene comprises (a) a chromium compound, (b) a metalated PNPNH compound, wherein the PNPNH compound is of the formula

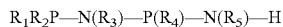

$$R_1R_2P-N(R_3)-P(R_4)-N(R_5)-H$$

wherein $R_1$, $R_2$, $R_3$, $R_4$ and $R_5$ are independently selected from halogen, amino, trimethylsilyl, $C_1$-$C_{10}$-alkyl, substituted $C_1$-$C_{10}$-alkyl, $C_6$-$C_{20}$-aryl and substituted $C_6$-$C_{20}$-aryl, or any cyclic derivative wherein at least one of the P or N atoms is a member of a ring system, the ring system being formed from two constituents of the PNPNH compound by substitution, and (c) an activator or cocatalyst.

In still another embodiment, a method for metalating a compound of the general formula

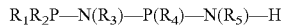

$$R_1R_2P-N(R_3)-P(R_4)-N(R_5)-H$$

wherein $R_1$, $R_2$, $R_3$, $R_4$ and $R_5$ are independently selected from halogen, amino, trimethylsilyl, $C_1$-$C_{10}$-alkyl, substituted $C_1$-$C_{10}$-alkyl, $C_6$-$C_{20}$-aryl and substituted $C_6$-$C_{20}$-aryl, or any cyclic derivative wherein at least one of the P or N atoms of the PNPN—H structure is a member of a ring system, the ring system being formed from one or more constituent compounds of the PNPNH-structure by substitution, the method comprises the steps of:

(i) dissolving the PNPNH compound in a solvent to obtain a solution;

(ii) metalating the PNPNH compound in the solution, and (iii) precipitating the metalated compound, separating from the solvent and optionally washing with the solvent.

A metalated compound, obtained by the foregoing method is also disclosed.

DETAILED DESCRIPTION

A process for oligomerization of ethylene, which allows use of a catalyst composition comprising a ligand that can be prepared in high purity in a safe and easy manner and results in a process with low wax/polymer formation rates is achieved by a process for oligomerization of ethylene, comprising subjecting a catalyst composition to a gas phase of ethylene and conducting an oligomerization, wherein the catalyst composition comprises (a) a chromium compound, (b) a metalated ligand (compound) as described herein, and (c) an activator or cocatalyst.

Preferably, the oligomerization is carried out a pressure of 1 to 200 bar, preferably 10 to 50 bar.

Preferably, the oligomerization is carried out at a temperature of from 10 to 200° C., preferably 20 to 100° C.

Preferably, the process is carried out continuously or batchwise.

Preferably, the mean residence time is from 20 minutes to 20 hours, preferably 1 to 4 hours.

A catalyst composition for oligomerization of ethylene comprises a chromium compound, a metalated ligand as described herein, and an activator or cocatalyst.

More preferably, the chromium compound is selected from organic or inorganic salts, coordination complexes, and organometallic complexes of Cr(II) or Cr(III).

Even more preferred, the chromium compound is selected from $CrCl_3(THF)_3$, Cr(III) acetyl acetonate, Cr(III)octanoate, chromium hexacarbonyl, Cr(III)-2-ethylhexanoate and (benzene)tricarbonyl-chromium.

Also preferred, the activator or co-catalyst is selected from trimethyl aluminum, triethyl aluminum, triisopropyl aluminum, triisobutyl aluminum, ethyl aluminum sesquichloride, diethyl aluminum chloride, ethyl aluminum dichloride, methyl aluminoxane (MAO), or a combination comprising at least one of the foregoing, preferably toluene.

A modifier can be present in the system, selected from (but not limited to) ammonium or phosphonium salts of the type $[H_4E]X$, $[H_3ER]X$, $[H_2ER_2]X$, $[HER_3]X$, or $[ER_4]X$ wherein E is N or P, X is Cl, Br or I, and R is alkyl, cycloalkyl, acyl, aryl, alkenyl, alkynyl, and the like. For example, dodecyltrimethylammonium chloride can be used, or tetraphenylphosphonium chloride.

A method for metalating a PNPNH compound of the general formula

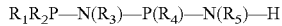

$$R_1R_2P-N(R_3)-P(R_4)-N(R_5)-H$$

wherein $R_1$, $R_2$, $R_3$, $R_4$ and $R_5$ are independently selected from halogen, amino, trimethylsilyl, $C_1$-$C_{10}$-alkyl, substituted $C_1$-$C_{10}$-alkyl, $C_6$-$C_{20}$-aryl and substituted $C_6$-$C_{20}$-aryl, or any cyclic derivative wherein at least one of the P or N atoms of the PNPN—H structure is a member of a ring system, the ring system being formed from one or more constituent compounds of the PNPNH-structure by substitution, the method comprising the steps of:

(i) dissolving the PNPNH compound in a solvent;

(ii) metalating the PNPNH compound, and (iii) isolating the metalated compound, for example by precipitating the metalated compound obtained in step b), separating from the solvent and optionally washing with the solvent.

Preferably, $R_1$, $R_2$, $R_3$, $R_4$, and $R_5$ are selected from chloro, amino, trimethylsilyl, methyl, ethyl, isopropyl, tert-butyl, phenyl, benzyl, tolyl, and xylyl.

More preferably, the PNPNH compound is selected from $(Ph)_2P-N(i-Pr)-P(Ph)-N(i-Pr)-H$, $(Ph)_2P-N(i-Pr)-P(Ph)-N(Ph)-H$, $(Ph)_2P-N(i-Pr)-P(Ph)-N(tert-butyl)-H$ and $(Ph)_2P-N(i-Pr)-P(Ph)-N(CH(CH_3)(Ph))-H$.

Preferably, metalating in step (ii) is achieved by adding an organometallic compound, a base, sodium metal, or potassium metal in an amount equivalent to or in excess of the molar concentration of the PNPNH compound into the solution obtained in step (i).

More preferred, metalation is achieved by adding n-butyl lithium, sec-butyl lithium, tert-butyl lithium, sodium cyclopentadienide, sodium hydride, sodium amide, alkyl- or aryl magnesium halides (Grignard reagents), sodium bis(trimethylsilyl) amide, dialkylmagnesium, diarylmagnesium, trialkylaluminium, dialkylzinc, sodium metal, or potassium metal, preferably n-butyllithium.

Finally, metalated compounds, obtainable by a method above, are described.

As used herein, the term PNPNH is to be understood to represent the general structure $R_1R_2P-N(R_3)-P(R_4)-N(R_5)-H$.

The metalated ligand disclosed herein may be abbreviated by "PNPN-M," with M being the metal used for metalation. This formula should be understood by a skilled person to comprise any compounds, such as $[PNPN-M]_2$, $[PNPN]_2M$, PNPNMR or PNPNMRR with R being any suitable alkyl or aryl substituent, clearly depending on the chemical requirements of the metalation reagent used. For example, metalation with lithium would result in a metalated ligand having the formula [PNPNLi]$_2$, or the use of chromium would result in a compound of [PNPN]$_2$Cr, or the use of dialkyl zinc would result in a structure of PNPNM alkyl.

As is to be understood, any cyclic derivative of the PNPNH compound can be utilized, wherein at least one of the P or N atoms of the PNPN-unit is a ring member, or any cyclic derivative wherein at least one of the P or N atoms of the PNPN—H structure is a member of a ring system, the ring system being formed from one or more constituent compounds of the PNPNH-structure by substitution, i.e., by formally eliminating per constituent compound either two whole groups $R_1$-$R_5$ (as defined above) or H, one atom from each of two groups $R_1$-$R_5$ (as defined above) or a whole group $R_1$-$R_5$ (as defined above) or H and an atom from another group $R_1$-$R_5$ (as defined above), and joining the formally so created valence-unsaturated sites by one covalent bond per constituent compound to provide the same valence as initially present at a given site. In an embodiment, the ring is formed by substitution of one or more, preferably two of the constituents of one PNPNH molecule. In other words, the cyclic derivative can include a ring system formed by removal of two of groups $R_1$-$R_5$ (as defined above) or H from one PNPNH molecule, with formation of a covalent bond in place of the groups. The cyclic derivative can include a ring system formed by removal of an atom from two of the groups $R_1$-$R_5$ (as defined above) or H from one PNPNH molecule, with formation of covalent bond in place of the atoms. Alternatively, the cyclic derivative can be formed by removal of one of the groups $R_1$-$R_5$ (as defined above) or H from one PNPNH molecule, and an atom from one of the groups $R_1$-$R_5$ (as defined above) or H from the same PNPNH molecule, with formation of a covalent bond in place of the removed group and the atom.

Suitable cyclic derivatives can be as follows.

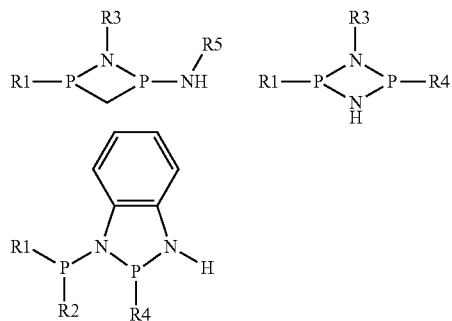

It is in general preferred, that the solvent is a non-polar solvent, preferably selected from aromatic and/or aliphatic solvents, preferably toluene, n-hexane, cyclohexane, and 1-hexene.

A preferred solvent for dissolving the PNPNH compound in step i) can be selected from toluene, n-hexane, cyclohexane, 1-hexene, or a combination comprising at least one of the foregoing, preferably toluene.

The separation in step iii) can be preferably achieved by filtration or centrifugation. The optional washing can be done with pure solvent.

It was surprisingly found that the metalated ligand itself can be used in a catalyst composition for the catalytic oligomerization of ethylene, i.e. without the necessity of reprotonation and further work-up of the ligand.

As shown below, the use of the metalated ligand instead of the PNPNH ligand may result in somewhat lower overall catalytic activities, albeit C6-selectivities and 1-hexene purities remain largely unaffected on a high level. The use of the metalated ligand has, however, the advantage of a very simple ligand purification procedure since the ligand purification takes places already during the precipitation of the metalated ligand material. The use of the metalated ligand leads to advantageously low wax/polymer formation rates in the oligomerization of ethylene and may be especially used whenever the achievement of the highest specific productivity is not of central importance.

Utilizing the metalated ligand obtained according to the present invention in the oligomerization of ethylene provides strong reduction of side-product wax and polyethylene formation, extension of oligomerization equipment's time on stream, less frequent shutdowns for purging, cleaning and maintenance, mitigation of equipment fouling, lower chances of operational upset conditions due to plugged equipment and, in summary, improvement of the plant operability in general.

As a further surprising fact, it was found that none of other possible candidates for the "key factors," i.e. key factors influencing a wax/polyethylene formation, showed any significant or discernable effect on polymer formation. Such further key factors can be, e.g., intrinsic mechanistic reasons linked to the metallocycle mechanism that is considered the origin of the high selectivity towards preferred oligomers, metallic impurities introduced as trace amounts of Fe, Ni, Ti, Zr, etc., along with the catalyst components, surface-induced heterogeneous reactions on the reactor's inner surface, chromium hydride species, radical polymerisation mechanisms or unfavourable oxidation states of chromium.

As already pointed out above, it was surprisingly found that by metalation of a PNPNH compound, the metalated compound can be easily separated from the impurities, as the metalated species regularly shows a poor solubility in the solvents to be typically used in the production process of the PNPNH compound and/or the oligomerization reaction. Preferred metalated species PNPN-M are those with M=Li, Mg, Na, K, Cr, Al and Zn. While specific examples of metalation reagents are given above, a PNPN—Cr compound can be preferentially obtained via transmetalation of the respective Mg-compound using CrCl$_2$(THF)$_2$ (under release of MgCl$_2$ and 2 THF). The Mg-metalated compound, in turn, can be obtained by reacting the PNPNH ligand with any metalating magnesium compound, such as Mg-alkyls or alkyl magnesium halides, such as butylethyl magnesium or isobutyl magnesium chloride.

Additional advantages and features of the present invention are now illustrated in the following example section.

EXAMPLES

Example 1

Ligand Preparation

Preparation of Bis(isopropyl-amino-)phenylphosphine (NPN)

To a stirred solution of isopropylamine (30 ml, 352 mmol) in diethylether (250 ml), dichlorophenylphosphine (9.63 ml, 71 mmol, dissolved in 50 ml diethylether) was added at 0° C. over a period of 30 min. After stirring for a total of 72 hrs the solution was filtrated. The residue was washed with diethylether and the solvent was removed in vacuum. The remaining oil was distilled at 0.2 Torr/76-78° C. to give a colorless liquid with 33% yield (5.3 g). $^{31}$P{H} NMR: 49.0 ppm.

Preparation of (Ph)$_2$PN(i-Pr)P(Ph)NH(i-Pr) (PNPN—H)

A solution of the NPN-species (2.4 g, 10.7 mmol) in tetrahydrofuran (10 ml) was added dropwise to a stirred solution of triethylamine (6 ml) and chlorodiphenylphosphine (2.36 g, 10.7 mmol) in tetrahydrofuran (40 ml) at −40° C. After additional stirring for 24 hrs at room temperature the triethylammonium salt was filtrated off and the residue was dissolved in n-hexane, filtrated again, and the solution was kept at −30° C. for crystallisation. Yield 52% (2.3 g, 5.6 mmol). $^{31}$P {H} NMR: 41.2, 68.4 (broad).

Example 2

Preparation of [Ph$_2$PN(i-Pr)P(Ph)N(i-Pr)—Li]$_2$

Ph$_2$PN(i-Pr)P(Ph)N(i-Pr)—H (8.70 g, 21.35 mmol) was dissolved in 15 ml of toluene. After cooling down to −78° C., n-butyllithium (12.8 ml, 2.5 M n-BuLi in n-heptane, 32.0 mmol) was added to the solution, causing the color to change immediately to orange/yellow. The solution was stirred for additional two hours at room temperature and a colorless solid precipitated. The precipitate was filtered and washed three times with 5 ml toluene. Remaining solvent was removed in vacuum to give a colorless powder. Yield: 6.73 g (76%). Molecular weight: 414.39 g/mol [C$_{24}$H$_{29}$LiN$_2$P$_2$]. Elementary analysis: calc.: C, 69.56%, H, 7.05 &, N, 6.76%. found: C, 69.25%, H, 7.06%, N, 6.87%. Melting point: 187-189° C. $^1$H NMR (THF-d$_8$) δ=7.50-7.57 (m, 6H, aryl-H), 7.20-7.34 (m, 6H, aryl-H), 7.02 (m, 2H, arom.), 6.93 (m, 1H, aryl-H), 3.70 (m, 1H, CHCH$_3$), 3.58 (m, 1H, CHCH$_3$), 1.39 (d, J=6.47 Hz, 3H, CHCH$_3$), 1.25 (d, J=6.23 Hz, 3H, CHCH$_3$), 1.22 (d, J=6.24 Hz, 3H, CHCH$_3$), 1.04 (d, J=6.55 Hz, 3H, CHCH$_3$); $_{13}$C-NMR (THF-d$_8$): δ=143.4, 142.0, 134.9, 133.4, 132.5, 131.5, 129.4, 128.6, 128.0, 127.9, 127.1, 125.2 (arom.), 54.6, 54.0 (CHCH$_3$), 31.0, 26.7 (CHCH$_3$); $^{31}$P{H} NMR (THF-d$_8$): δ=40.6 (br), 100.1 pp, (d, $^2$J$_{P-P}$=24.6 Hz).

Additional metalated ligands were produced by use of zinc, magnesium, chromium, and aluminium metalation agents.

Example 3

Preparation of Ph$_2$PN(i-Pr)P(Ph)N(i-Pr)ZnEt

Ph$_2$PN(i-Pr)P(Ph)(i-Pr)—H (1.00 g, 2.45 mmol) was dissolved in 40 mL of diethylether. At room temperature a solution of diethylzinc (2.0 mL, 1.5 M ZnEt$_2$ in toluene, 3.00 mmol) was added to the solution. After stirring for 12 h the solution was condensed to 20 mL. Cooling to −30° C. results in a colourless solid. Yield: 0.800 g (65%). Molecular weight: 501.92 g/mol [C$_{26}$H$_{34}$N$_2$P$_2$Zn]. Anal. Calcd: C, 62.22; H, 6.83; N, 5.58; P, 12.34. Found: C, 62.71; H, 6.80; N, 6.03; P, 12.29. Melting point: 95° C. $^1$H-NMR (C$_6$D$_6$): δ=7.75-7.68 (m, 2H, aryl-H), 7.65-7.56 (m, H, aryl-H), 7.44-7.35 (m, 2H, aryl-H), 7.26-7.16 (m, 2H, aryl-H), 7.10-6.90 (m, 8H, aryl-H), 4.03-3.88 (m, H, CHCH$_3$), 3.66-3.53 (m, H, CHCH$_3$), 1.56-1.39 (m, 9H, CHCH$_3$) 1.38-1.31 (m, 3H, CH$_2$CH$_3$), 1.31-1.27 (m, 3H CHCH$_3$), 0.73-0.62 (m, 2H, CH$_2$CH$_3$); $^{13}$C-NMR (C$_6$D$_6$): δ=151.3, 134.1, 133.4, 132.2, 130.9, 130.1, 129.5, 128.5, 128.1 (arom.), 51.6, 50.2 (CHCH$_3$), 31.0, 29.9, 26.5, 24.4 (CHCH$_3$), 12.8 (CH$_2$CH$_3$), 2.9 (CH$_2$CH$_3$); $^{31}$P {H} NMR (C$_6$D$_6$): δ=87.50 (d, J=16.5 Hz), 28.00 (d, J=16.5 Hz).

Example 4

Preparation of [Ph$_2$PN(i-Pr)P(Ph)N(i-Pr)]$_2$Mg (Ph$_2$PN(i-Pr)P(Ph)(i-Pr)—H (4.00 g, 9.79 mmol) was dissolved in 50 mL of diethylether. At room temperature a solution of n-butylethylmagnesium (5.5 mL, 0.9 M n-BuEtMg in heptane, 4.95 mmol) was added to the solution. The solution was stirred for an additional 2 h. After cooling to −30° C. colourless crystals with satisfying elementary analysis were obtained. Yield: 3.70 g (90%). Molecular weight: 839.20 g/mol [C$_{48}$H$_{58}$MgN$_4$P$_4$]. Elementary analysis: calc.: C, 68.70; H, 6.97; N, 6.68. found: C, 68.93; H, 7.07; N, 6.91. Melting point: 202° C. $^1$H NMR (C$_6$D$_6$): δ=6.83-7.66 (m, 30H, aryl-H), 3.54-3.62 (m, 2H, CHCH$_3$), 3.38-3.48 (m, 2H, CHCH$_3$), 1.51 (d, J=6.5 Hz, 6H, CHCH$_3$), 1.19 (d, J=6.5 Hz, 6H, CHCH$_3$), 1.15 (d, J=6.5 Hz, 6H, CHCH$_3$), 1.10 (m, 6H, CHCH$_3$); $^{13}$C-NMR (C$_6$D$_6$): δ=143.4, 142.0, 134.9, 133.4, 132.5, 131.5, 129.4, 128.6, 128.0, 127.9, 127.1, 125.2 (arom.), 52.0, 51.5 (CHCH$_3$), 29.5, 28.6, 25.9, 24.1 (CHCH$_3$); $^{31}$P {H} NMR (C$_6$D$_6$) δ=87.05 (tr, J=10.4 Hz), 28.32 (tr, J=10.4 Hz).

Example 5

Preparation of [Ph$_2$PN(i-Pr)P(Ph)N(i-Pr)]$_2$Cr

Ph$_2$PN(i-Pr)P(Ph)(i-Pr)—H (4.00 g, 9.79 mmol) was dissolved in 40 mL of toluene. At room temperature a solution of n-butyl-ethylmagnesium (5.5 mL, 0.9 M n-BuEtMg in heptane, 4.95 mmol) was added to the solution. The solution was stirred for an additional two hours and thereafter filtered to CrCl$_2$(THF)$_2$ (1.31 g, 4.90 mmol). Stirring for two days results in a red-brownish suspension. After filtration and concentrating to 10 mL dark crystals were obtained upon standing at −78° C. Satisfying elementary analysis was obtained by washing the powdered crystals with pentane. Yield: 2.76 g (65%). Molecular weight: 866.89 g/mol [C$_{48}$H$_{58}$CrN$_4$P$_4$]. Anal. Calcd: C, 66.50; H, 6.74; Cr, 6.00; N, 6.46; P, 14.29. Found: C, 66.28; H, 6.43; Cr, 6.20; N, 6.31; P, 14.69. Melting point: 161° C. (decomposition).

Example 6

Preparation of Ph$_2$PN(i-Pr)P(Ph)N(i-Pr)-AlEt$_2$.AlEt$_3$

Et$_3$Al (1.9 M Et$_3$Al in toluene, 10.0 ml, 19 mmol) was added to (Ph$_2$PN(i-Pr)P(Ph)(i-Pr)—H (3.7 g, 9.06 mmol) dissolved in toluene (10 mL). The solution was heated for 28 h at 50° C. After removal of the solvent in vacuum colorless oil remained which was treated with 5 ml n-hexane. By evaporation of the solvent in vacuum a colorless residue remained. Recrystallization from n-hexane yields a colorless material. Molecular weight: 606.72 g/mol [C$_{34}$H$_{54}$Al$_2$N$_2$P$_2$]. Yield: 4.86 g (95%). Elementary analysis: calc.: C, 67.31, H, 8.97, N, 4.62. found: C, 67.08, H, 8.87, N, 4.46. Melting point: 78° C. (dec.). $^1$H-NMR (C$_6$D$_6$) δ=−0.47 (m, 1H, J=8.1 Hz, AlC(H)HCH$_3$), −0.21 (m, 1H, J=8.1 Hz, AlC(H)HCH$_3$), 0.03 (m, 1H, J=8.1 Hz, AlC(H)HCH$_3$), 0.16 (m, 1H, J=8.1 Hz, AlC(H)HCH$_3$), 0.47 (q, 6H, J=8.1 Hz, Al(CH$_2$CH$_3$)$_2$), 0.90 (tr, 3H, J=8.1 Hz, AlCH$_2$CH$_3$), 1.06 (d, 3H, J=6.7 Hz, CHCH$_3$), 1.24 (tr, 3H, J=8.1 Hz, AlCH$_2$CH$_3$), 1.31 (d, 3H, J=6.7 Hz, CHCH$_3$); 1.42 (tr, 3H, J=8.1 Hz, AlCH$_2$CH$_3$), 1.45 (d, 3H, J=6.7 Hz, CHCH$_3$), 1.53 (d, 3H, J=6.7 Hz, CHCH$_3$), 3.77 (m, 1H, CHCH$_3$), 4.16 (m, 1H, CHCH$_3$), 6.94-7.61 (m, 15H, C$_6$H$_5$); $^{13}$C-NMR (CDCl$_3$): δ=2.2, 3.0 (CH$_2$CH$_3$), 9.6, 10.6 (CH$_2$CH$_3$), 24.6, 25.5, 27.4, 28.5 (d, CHCH$_3$), 52.3, 52.7

(CHCH$_3$), 127.6, 128.7, 128.9, 129.8, 130.5, 130.9, 132.1, 132.5, 132.7, 134.6, 141.9, 142.1 (C$_6$H$_5$); $^{31}$P {H} NMR (C$_6$D$_6$) δ=31.55 (d, $^1J_{P\text{-}P}$=11.6 Hz), 91.00 (d, $^1J_{P\text{-}P}$=11.6 Hz).

The metalation of a specific PNPNH compound is shown in the equation below, wherein "iPr" is isopropyl.

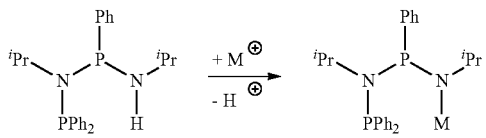

Example 7

A standard ethylene oligomerization (trimerization to 1-hexene) was carried out and ligands prepared as above were utilized.

The average activity, C6-yield, 1-C6 in C6, C10-yield and PE/wax formation were measured. The results are given in Table 1.

In Table 1, LAO product distribution and average activity depending on the metal of the ligands Ph$_2$PN(i-Pr)P(Ph)N(i-Pr)M, in comparison to the protonated ligand Ph$_2$PN(i-Pr)P(Ph)N(i-Pr)H is shown, where the system is: ligand, Cr(acac)$_3$, modifier [PPh$_4$]Cl, TEA in toluene. The process conditions were: T=50° C., p=30 bar, t=60 min, [Cr]=0.3 mmol/L, [Ligand]/[Cr]=1.25, [Al]/[Cr]=25, [Cl]/[Cr]=5.

TABLE 1

| Ligand | Average activity over 1 hr [kg/g$_{Cr}$·h)] | C6-Yield [wt. %] | 1-C6 in C6 [wt. %] | C10-Yield [wt-%] | Polymer [wt. %] |
|---|---|---|---|---|---|
| Ph$_2$PN(i-Pr)P(Ph)N(i-Pr)H | 40.1 | 91.2 | 99.0 | 5.8 | 0.20 |
| [Ph$_2$PN(i-Pr)P(Ph)N(i-Pr)—Li]$_2$ | 28.9 | 92.2 | 99.0 | 4.9 | 0.03 |
| Ph$_2$PN(i-Pr)P(Ph)N(i-Pr)ZnEt | 12.7 | 91.7 | 89.9 | 5.6 | 0.20 |
| [Ph$_2$PN(i-Pr)P(Ph)N(i-Pr)]$_2$Mg | 16.7 | 91.5 | 89.9 | 6.0 | 0.10 |
| [Ph$_2$PN(i-Pr)P(Ph)N(i-Pr)]$_2$Cr*[1] | 14.2 | 90.8 | 99.0 | 4.8 | 0.05 |
| Ph$_2$PN(i-Pr)P(Ph)N(i-Pr)—AlEt$_2$·AlEt$_3$*[2] | 22.3 | 91.7 | 99.0 | 5.3 | 0.05 |

*[1]0.1875 mmol/L [Ph$_2$PN(i-Pr)P(Ph)N(i-Pr)]$_2$Cr and 0.1125 mmol/L (Cr(acac)$_3$ were added to meet the process condition requirements
*[2]6.75 mmol/L TEA was added to meet the process condition requirements.

In summary, disclosed herein is a process for oligomerization of ethylene, comprising contacting a catalyst composition with a gas phase of ethylene under conditions effective to oligomerize the ethylene, preferably a pressure of 1 to 200 bar, more preferably 10 to 50 bar, at a temperature of from 10 to 200° C., more preferably 20 to 100° C., preferably for a mean residence time is from 20 minutes to 20 hours, preferably 1 to 4 hours, wherein the catalyst composition comprises a chromium compound, preferably wherein the chromium compound is selected from organic or inorganic salts, coordination complexes, organometallic complexes of Cr(II) or Cr(III), or a combination comprising at least one of the foregoing, more preferably wherein the chromium compound is CrCl$_3$(THF)$_3$, Cr(III)acetyl acetonate, Cr(III)octanoate, chromium hexacarbonyl, Cr(III)-2-ethyl-hexanoate and (benzene)tricarbonyl-chromium, or a combination comprising at least one of the foregoing; a metalated PNPNH compound, wherein the PNPNH compound is of the formula

R$_1$R$_2$P—N(R$_3$)—P(R$_4$)—N(R$_5$)—H wherein R$_1$, R$_2$, R$_3$, R$_4$ and R$_5$ are independently selected from halogen, amino, trimethylsilyl, C$_1$-C$_{10}$-alkyl, substituted C$_1$-C$_{10}$-alkyl, C$_6$-C$_{20}$-aryl and substituted C$_6$-C$_{20}$-aryl, or any cyclic derivative wherein at least one of the P or N atoms of the PNPN—H structure is a member of a ring system, the ring system being formed from one or more constituent compounds of the PNPNH-structure by substitution, preferably any cyclic derivative wherein at least one of the P or N atoms is a member of a ring system, the ring system being formed from two constituents of the same PNPNH compound by substitution, preferably wherein R$_1$, R$_2$, R$_3$, R$_4$ and R$_5$ are selected from chloro, amino, trimethylsilyl, methyl, ethyl, isopropyl, tert-butyl, phenyl, benzyl, tolyl and xylyl, more preferably wherein the PNPNH compound is (Ph)$_2$P—N(i-Pr)—P(Ph)-N(i-Pr)—H, (Ph)$_2$P—N(i-Pr)—P(Ph)-N(Ph)-H, (Ph)$_2$P—N(i-Pr)—P(Ph)-N(tert-butyl)-H, (Ph)$_2$P—N(i-Pr)—P(Ph)-N(CH(CH$_3$)(Ph))-H, or a combination comprising at least one of the foregoing; and an activator or cocatalyst, preferably trimethyl aluminum, triethyl aluminum, triisopropyl aluminum, triisobutyl aluminum, ethyl aluminum sesquichloride, diethyl aluminum chloride, ethyl aluminum dichloride, methyl aluminoxane, or a combination comprising at least one of the foregoing.

A catalyst composition for oligomerization of ethylene comprises a chromium compound, preferably wherein the chromium compound is selected from organic or inorganic salts, coordination complexes, organometallic complexes of C(II) or Cr(III), or a combination comprising at least one of the foregoing, more preferably wherein the chromium compound is CrCl$_3$(THF)$_3$, Cr(III)acetyl acetonate, Cr(III)octanoate, chromium hexacarbonyl, Cr(III)-2-ethyl-hexanoate and (benzene)tricarbonyl-chromium, or a combination comprising at least one of the foregoing; a metalated PNPNH compound, wherein the PNPNH compound is of the formula

R$_1$R$_2$P—N(R$_3$)—P(R$_4$)—N(R$_5$)—H wherein R$_1$, R$_2$, R$_3$, R$_4$ and R$_5$ are independently selected from halogen, amino, trimethylsilyl, C$_1$-C$_{10}$-alkyl, substituted C$_1$-C$_{10}$-alkyl, C$_6$-C$_{20}$-aryl and substituted C$_6$-C$_{20}$-aryl, or any cyclic derivative wherein at least one of the P or N atoms of the PNPN—H structure is a member of a ring system, the ring system being formed from one or more constituent compounds of the PNPNH-structure by substitution, preferably any cyclic derivative wherein at least one of the P or N atoms is a member of a ring system, the ring system being formed from two constituents of the same PNPNH compound by substitution, preferably wherein R$_1$, R$_2$, R$_3$, R$_4$ and R$_5$ are selected from chloro, amino, trimethylsilyl, methyl, ethyl, isopropyl, tert-butyl, phenyl, benzyl, tolyl and xylyl, more preferably wherein the PNPNH compound is (Ph)$_2$P—N(i-Pr)—P(Ph)-N(i-Pr)—H, (Ph)$_2$P—N(i-Pr)—P(Ph)-N(Ph)-H, (Ph)$_2$P—N(i-Pr)—P(Ph)-N(tert-butyl)-H, (Ph)$_2$P—N(i-

Pr)—P(Ph)-N(CH(CH$_3$)(Ph))-H, or a combination comprising at least one of the foregoing; and an activator or cocatalyst, preferably trimethyl aluminum, triethyl aluminum, triisopropyl aluminum, triisobutyl aluminum, ethyl aluminum sesquichloride, diethyl aluminum chloride, ethyl aluminum dichloride, methyl aluminoxane, or a combination comprising at least one of the foregoing.

A method for metalating a compound of the general formula

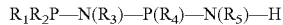

wherein R$_1$, R$_2$, R$_3$, R$_4$ and R$_5$ are independently selected from halogen, amino, trimethylsilyl, C$_1$-C$_{10}$-alkyl, substituted C$_1$-C$_{10}$-alkyl, C$_6$-C$_{20}$-aryl and substituted C$_6$-C$_{20}$-aryl, or any cyclic derivative wherein at least one of the P or N atoms of the PNPN—H structure is a member of a ring system, the ring system being formed from one or more constituent compounds of the PNPNH-structure by substitution, preferably any cyclic derivative wherein at least one of the P or N atoms is a member of a ring system, the ring system being formed from two constituents of the same PNPNH compound by substitution, preferably wherein R$_1$, R$_2$, R$_3$, R$_4$ and R$_5$ are selected from chloro, amino, trimethylsilyl, methyl, ethyl, isopropyl, tert-butyl, phenyl, benzyl, tolyl and xylyl, more preferably wherein the PNPNH compound is (Ph)$_2$P—N(i-Pr)—P(Ph)-N(i-Pr)—H, (Ph)$_2$P—N(i-Pr)—P(Ph)-N(Ph)-H, (Ph)$_2$P—N(i-Pr)—P(Ph)-N(tert-butyl)-H, (Ph)$_2$P—N(i-Pr)—P(Ph)-N(CH(CH$_3$)(Ph))-H, or a combination comprising at least one of the foregoing wherein the method comprises the steps of: dissolving the PNPNH compound in a solvent to obtain a solution; metalating the PNPNH compound in the solution, and precipitating the metalated compound, separating from the solvent and optionally washing with the solvent.

The method according to any of the preceding claims 10-12, preferably wherein the metalating is by adding, into the solution, an organometallic compound, a metal-containing base, sodium metal, or potassium metal, in an amount equivalent to or in excess of the molar concentration of the PNPNH compound, more preferably wherein metalation is achieved by adding n-butyl lithium, sec-butyl lithium, tert-butyl lithium, sodium cyclopentadienide, sodium hydride, sodium amide, alkyl- or aryl magnesium halides (Grignard reagents), sodium bis(trimethylsilyl) amide, dialkylmagnesium, diarylmagnesium, trialkylaluminium, dialkylzinc, sodium metal, or potassium metal, preferably n-butyllithium, or a combination comprising at least one of the foregoing.

The singular forms "a," "an," and "the" include plural referents unless the context clearly dictates otherwise. "Or" means "and/or." Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

The features disclosed in the foregoing description, in the claims and in the drawings may, both separately and in any combination thereof, be material for realizing the invention in diverse forms thereof.

What is claimed is:

1. A process for oligomerization of ethylene, comprising contacting a catalyst composition with a gas phase of ethylene under conditions effective to oligomerize the ethylene, wherein the catalyst composition comprises:
    (a) a chromium compound,
    (b) a metalated PNPNH compound comprising a metalated ligand of the formula PNPN-M or [PNPN]$_2$Cr, wherein the PNPNH compound is of the formula

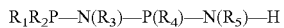

wherein R$_1$, R$_2$, R$_3$, R$_4$ and R$_5$ are independently selected from halogen, amino, trimethylsilyl, C$_1$-C$_{10}$-alkyl, substituted C$_1$-C$_{10}$-alkyl, C$_6$-C$_{20}$-aryl and substituted C$_6$-C$_{20}$-aryl, or any cyclic derivative wherein at least one of the P or N atoms of the PNPNH structure is a member of a ring system, the ring system being formed from one or more constituent compounds of the PNPNH-structure by substitution,
wherein M is Mg, Na, K, or Zn, and
    (c) an activator or cocatalyst.

2. The process of claim 1, further comprising an ammonium or phosphonium salt of the formula [H$_4$E]X, [H$_3$ER]X, [H$_2$ER$_2$]X, [HER$_3$]X, or [ER$_4$]X wherein E is N or P, X is Cl, Br or I, and each R is independently C$_1$-C$_{22}$-alkyl, C$_3$-C$_{10}$-cycloalkyl, C$_1$-C$_{22}$-acyl, C$_6$-C$_{30}$-aryl, C$_2$-C$_{22}$-alkenyl, or C$_2$-C$_{22}$-alkynyl.

3. The process according to claim 1, wherein the oligomerization is carried out a pressure of 1 to 200 bar.

4. The process according to claim 1, wherein the oligomerization is carried out at a temperature of from 10 to 200° C.

5. The process according to claim 1, wherein the oligomerization is carried out at a residence time of from 20 minutes to 20 hours.

6. A catalyst composition for oligomerization of ethylene comprising:
    (a) a chromium compound,
    (b) a metalated PNPNH compound comprising a metalated ligand of the formula PNPN-M or [PNPN]$_2$Cr, wherein the PNPNH compound is of the formula

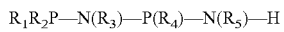

wherein R$_1$, R$_2$, R$_3$, R$_4$ and R$_5$ are independently selected from halogen, amino, trimethylsilyl, C$_1$-C$_{10}$-alkyl, substituted C$_1$-C$_{10}$-alkyl, C$_6$-C$_{20}$-aryl and substituted C$_6$-C$_{20}$-aryl, or any cyclic derivative wherein at least one of the P or N atoms is a member of a ring system, the ring system being formed from two constituents of the PNPNH compound by substitution, wherein M is Mg, Na, K, or Zn, and
    (c) an activator or cocatalyst.

7. The catalyst composition according to claim 6, wherein the chromium compound is selected from organic or inorganic salts, coordination complexes, organometallic complexes of Cr(II) or Cr(III), or a combination thereof.

8. The catalyst composition according to claim 6, wherein the chromium compound is CrCl$_3$(THF)$_3$, Cr(III)acetyl acetonate, Cr(III)octanoate, chromium hexacarbonyl, Cr(III)-2-ethyl-hexanoate and (benzene)tricarbonyl-chromium, or a combination thereof.

9. The catalyst composition according to claim 6, wherein the activator or co-catalyst is selected from trimethyl aluminum, triethyl aluminum, triisopropyl aluminum, triisobutyl aluminum, ethyl aluminum sesquichloride, diethyl aluminum chloride, ethyl aluminum dichloride, methyl aluminoxane, or a combination thereof.

10. The catalyst composition according to claim 6, further comprising an ammonium or phosphonium salt of the formula [H$_4$E]X, [H$_3$ER]X, [H$_2$ER$_2$]X, [HER$_3$]X, or [ER$_4$]X wherein E is N or P, X is Cl, Br or I, and each R is independently C$_1$-C$_{22}$-alkyl, C$_3$-C$_{10}$-cycloalkyl, C$_1$-C$_{22}$-acyl, C$_6$-C$_{30}$-aryl, C$_2$-C$_{22}$-alkenyl, or C$_2$-C$_{22}$-alkynyl.

11. The catalyst composition according to claim 10, wherein the chromium compound is Cr(III)acetyl acetonate, the PNPNH compound is selected from (Ph)$_2$P—N(i-Pr)—P(Ph)-N(i-Pr)—H, (Ph)$_2$P—N(i-Pr)—P(Ph)-N(Ph)-H, (Ph)$_2$P—N(i-Pr)—P(Ph)-N(tert-butyl)-H and (Ph)$_2$P—N(i-Pr)—P(Ph)-N(CH(CH$_3$)(Ph))-H, the activator or co-catalyst is triethyl aluminium, and the phosphonium salt is tetraphenylphosphonium chloride.

12. The catalyst composition according to claim 11, wherein the metalated ligand is of the formula [PNPN]$_2$Cr.

13. The catalyst composition according to claim 11, wherein the metalated ligand is of the formula PNPN-M and M is Mg.

\* \* \* \* \*